United States Patent [19]

Boxhoorn et al.

[11] Patent Number: 4,806,518
[45] Date of Patent: Feb. 21, 1989

[54] PROCESS FOR THE PREPARATION OF A SILVER-CONTAINING ETHYLENE OXIDE CATALYST AND THE CATALYST PREPARED BY THE PROCESS

[75] Inventors: Gosse Boxhoorn; Peter J. Schoenmakers; Otto M. Velthuis, all of Amsterdam, Netherlands

[73] Assignee: Shell Oil Company, Houston, Tex.

[21] Appl. No.: 49,901

[22] Filed: May 15, 1987

[30] Foreign Application Priority Data

May 28, 1986 [GB] United Kingdom ................ 8612951

[51] Int. Cl.$^4$ ........................ B01J 23/04; B01J 23/50; B01J 27/10; B01J 27/12
[52] U.S. Cl. ..................................... 502/231; 502/348
[58] Field of Search ........................ 502/347, 348, 231

[56] References Cited

U.S. PATENT DOCUMENTS

| | | | |
|---|---|---|---|
| 4,168,247 | 9/1979 | Hayden et al. | 502/347 |
| 4,414,135 | 11/1983 | Nojiri | 502/224 |
| 4,575,494 | 3/1986 | Young et al. | 502/348 X |

Primary Examiner—W. J. Shine

[57] ABSTRACT

A process for the preparation of a silver-containing catalyst suitable for the oxidation of ethylene to ethylene oxide which comprises:
(a) mixing alumina with a salt of an alkali metal and with aluminum fluoride or aluminum chloride,
(b) calcining the mixture to obtain an alkali enriched alumina carrier,
(c) applying a silver compound to the alkali enriched alumina carrier and converting said silver compound to metallic silver.

23 Claims, No Drawings

PROCESS FOR THE PREPARATION OF A SILVER-CONTAINING ETHYLENE OXIDE CATALYST AND THE CATALYST PREPARED BY THE PROCESS

FIELD OF THE INVENTION

The invention relates to a process for the preparation of a silver-containing catalyst suitable for the preparation of ethylene oxide, to the prepared catalyst and to the use of the catalyst for the preparation of ethylene oxide.

BACKGROUND OF THE INVENTION

It is generally known for a silver-containing catalyst to be employed in the preparation of ethylene oxide from ethylene. See for example U.S. Pat. No. 3,962,136 and also the literature cited therein. In order to obtain improved silver catalysts, efforts have been directed for many years towards modifying the silver catalysts with the aid of promoters. For example, the above-mentioned U.S. Pat. No. 3,962,136 describes a process in which a silver compound is applied to a carrier, after which the applied silver compound is reduced to silver and in which additionally a promoter in the form of potassium oxide, rubidium oxide or cesium oxide or a mixture thereof is present on the carrier.

In co-pending U.S. application Ser. No. 874,913, filed June 16, 1986, now abandoned, is described a process for the preparation of a silver-containing catalyst suitable for the oxidation of ethylene to ethylene oxide, whereby a silver compound and, if desired, a promoter are applied to an alkali enriched carrier, after which the silver compound is reduced to metallic silver, and in which process the alkali enriched carrier has been prepared by mixing an aluminum compound with a salt of an alkali metal and by calcining the mixture. The obtained silver catalyst has a good stability.

I has now been found that silver catalysts may be prepared with even better stability by using the process of the instant invention.

SUMMARY OF THE INVENTION

The invention relates to a process for the preparation of a silver-containing catalyst suitable for the oxidation of ethylene to oxide which comprises (a) mixing an aluminum oxide with a salt of an alkali metal and with aluminum fluoride and/or aluminum chloride, (b) calcining the mixture to obtain an alkali enriched alumina carrier, (c) applying a silver compound to the alkali enriched alumina carrier and converting said silver compound to metallic silver. The catalysts thus prepared have improved stabilities over catalysts prepared without the use of aluminum halide to prepare the support.

DESCRIPTION OF THE PREFERRED EMBODIMENTS

The aluminum oxides can be several modifications of aluminum oxide, which when calcined at between 1200° C. and 1700° C. generally produce alpha-aluminum oxide, such as gamma-aluminum oxide. Another possibility is to choose a hydrated aluminum oxide, such as boehmite, which via gamma-aluminum oxide produces alpha-aluminum oxide.

The salts of the alkali metals may be, for example, fluorides, nitrates, chlorides or sulphates. The metals are lithium, sodium, potassium, rubidium or cesium. Preferably, potassium, rubidium or cesium salts are used. Cesium salts are preferred. Cesium fluoride and cesium chloride are particularly preferred.

The quantity of salt of the alkali metal that is mixed with the alumina is chosen such that the atom ratio of the alkali metal/aluminum (oxide) is between 0.0001 and 0.1 preferably between 0.001 and 0.01. The atomic ratio of aluminum(halide/aluminum(oxide) ranges from 0.01 to 0.1.

For the preparation of the alkali enriched alumina carrier, preferably the alumina is mixed with water and an alkali metal salt and aluminum fluoride or aluminum chloride, the mixture thus obtained is extruded to shaped carrier particles which are subsequently calcined. The calcination can take place in one or more steps, depending on the choice of starting material. In general, sufficient water is added to make the mixture extrudable. The extrudable paste obtained is then extruded in an extruder to form shaped pieces. These shaped pieces are heated, during which water still present is evaporated. The solid pieces are then calcined. In order to prepare the alpha aluminum oxide modification, calcination up to a temperature of between 1200° C. and 1700° C. is necessary. Suitable starting materials are powders of gamma-aluminum oxide, alpha-aluminum oxide, alpha-aluminum oxide monohydrate, alpha-aluminum oxide trihydrate and beta-aluminum oxide monohydrate, which are sintered during the calcination, with fusion of the powder particles taking place. The heating and calcination also changes the crystal structure: the cubic structure of gamma aluminum oxide changes into the hexagonal structure of alpha aluminum oxide.

The effective catalyst surface area can vary from between 0.2 and 5 $m^2/g$. It has also been found that for the alpha-aluminum oxide, the alkali metal (e.g., cesium) is present at the surface at a concentration higher than is to be expected on the basis of the weighed-out quantity of alkali metal.

In order to prepare the catalyst, the alkali enriched alumina carrier is impregnated with a solution of a silver compound, sufficient to apply, as wished, 1 to 25 weight per cent of silver, calculated on the weight of the total catalyst, on the carrier. The impregnated carrier is separated from the solution, if necessary and the precipitated silver compound is reduced to metallic silver. It may be that the whole solution is impregnated on the carrier.

Preferably, a promoter is added, for example one or more of the alkali metals: potassium, rubidium or cesium. The promoters can be applied on the carrier before, during or after the impregnation with the silver compound. The promoter can also be applied on the carrier after the silver compound has been reduced to silver.

In general, the carrier is mixed with an aqueous solution of a silver salt or a silver complex, so that the carrier is impregnated with this solution, after which the carrier may be separated from the solution if necessary and subsequently dried. The impregnate carrier is then heated to a temperature of between 100° C. and 400° C. for a period necessary for the silver salt (or complex) to decompose and form a finely distributed layer of metallic silver which adheres to the inner and outer surfaces. Temperatures above 400° C. should be avoided, since then sintering of the silver particles takes place.

Various methods are known for adding the silver. The carrier can be impregnated with an aqueous solution of silver nitrate, then dried, after which the silver nitrate is reduced with hydrogen or hydrazine. The carrier can also be impregnated with an ammoniacal solution of silver oxalate or silver carbonate, the deposition of silver metal being effected by thermally decomposing the salt. Special solutions of silver salt with certain solubilizing and reducing agents, such as combinations of vicinal alkanolamines, alkydiamines and ammonia also serve the purpose.

The quantity of added promoter is generally between 20 and 1000 parts by weight of an alkali metal, such as potassium, rubidium or cesium (as metal) per million parts by weight of total catalyst. 50 to 300 parts by weight of alkali metal is particularly suitable. Suitable compounds to serve as starting material for promoters are, for example, nitrates, oxalates, carboxylic acid salts or hydroxides. The most preferred promoter is cesium.

Some excellent methods are known for adding the alkali metals in which these metals can be applied at the same time as the silver. Suitable alkali metal salts are generally salts which are soluble in the silver-depositing liquid phase. Besides the above-mentioned salts, it is also worth mentioning nitrates, chlorides, iodides, bromides, bicarbonates, acetates, tartrates, lactates and isopropoxides. The use of alkali metal salts which react with the silver present in the solution and thus cause silver salts to be prematurely precipitated from an impregnating solution should, however, be avoided. For example, potassium chloride should not be used for impregnating techniques in which an aqueous silver nitrate solution is used, but potassium nitrate can be used instead. Potassium chloride can be suitably used in a process in which an aqueous solution of silver amine complexes, from which no silver chloride will precipitate, is used.

In addition, the amount of alkali metal deposited on the carrier can be adjusted within certain limits by washing out a part of the alkali metal with, preferably, anhydrous methanol or ethanol. This method is employed subsequently if the concentration of the applied alkali metal is found to be too high. The temperatures, contact times and the drying with gases can be adjusted. Care should be taken to ensure that no traces of alcohol remain in the carrier. High temperature heat treatments can also be utilized to remove or otherwise inactivate a portion of the alkali metal deposited on the surface of the carrier.

A preferably employed process consists of the carrier being impregnated with an aqueous solution containing both alkali metal salt and silver salt, the impregnating solution being composed of a silver salt of a carboxylic acid, an organic amine, a salt of potassium, rubidium or cesium and an aqueous solvent. For example, a potassium-containing silver oxalate solution can be prepared in two ways. Silver oxide can be reacted with a mixture of ethylene diamine and oxalic acid giving a solution containing a silver oxalate ethylene diamine complex, to which a certain amount of potassium and possibly other amines such as ethanolamine is added. Silver oxalate can also be precipitated from a solution of potassium oxalate and silver nitrate, the silver oxalate thus obtained then being repeatedly washed in order to remove the attached potassium salts until the desired potassium content is obtained. The potassium-containing silver oxalate is then solubilized with ammonia and/or amine. Solutions containing rubidium and cesium can also be prepared in this way. The thus impregnated carriers are then heated to a temperature of between 100° C. and 400° C., preferably between 125° C. and 325° C.

It should be noted that, irrespective of the nature of the silver in the solution before the precipitation onto the carrier, reference is always made to reduction to metallic silver, whereas it could also be referred to as decomposition on heating. It is preferred to think in terms of reduction, since positively charged Ag ions are converted into metallic Ag. The reduction times can be simply adapted to the starting materials employed.

As mentioned above, a promoter is preferably added to the silver. Cesium is the most preferred promoter in view of the fact that its selectivity for ethylene oxide has been found to be the highest in comparison with the use of potassium or rubidium as promoter.

Thus, this invention relates to a catalyst for the production of ethylene oxide from ethylene and molecular oxygen which comprises about 1-25 wt % silver (basis total catalyst) and about 20-1000 ppm of cesium promoter (basis total catalyst) supported on a carrier wherein the improvement comprises preparing the carrier by a process which comprises:

(a) mixing an anhydrous or hydrated alumina with water, cesium fluoride, nitrate, chloride or sulphate and with aluminum fluoride or aluminum chloride, (b) shaping the mixture of (b), (c) calcining the shaped mixture of (b) at a temperature ranging from about 1200° C. to about 1700° C. to obtain an alkali enriched alumina carrier, (d) applying a silver compound and a cesium promoter to the alkali enriched alumina carrier and converting said silver compound to metallic silver.

The silver catalysts prepared by the process according to the present invention appear to be particularly stable catalysts for the direct catalytic oxidation of ethylene to ethylene oxide with the aid of molecular oxygen. The conditions for carrying out the oxidation reaction in the presence of the silver catalysts according to the invention are fairly similar to those already described in the literature. This applies to, for suitable temperatures, pressures, residence times, diluents such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing either recirculating treatments or successive conversions in different reactors to enhance the yield of ethylene oxide, as well as any other special conditions which may be chosen for processes for the preparation of ethylene oxide. Usually, the pressures employed vary from about atmospheric pressure to about 35 bar. Higher pressures are, however, by no means excluded. The molecular oxygen employed as reactant can be obtained from conventional sources. The oxygen feed can consist of substantially pure oxygen, of a concentrated oxygen stream consisting of a large amount of oxygen with smaller amounts of one or more diluents, such as nitrogen, argon, etc., or of another oxygen-containing stream, such as air.

In a preferably employed application of the silver catalysts according to the present invention, ethylene oxide is prepared by contacting an oxygen-containing gas that has been separated from air and that contains not less than 95% oxygen with ethylene in the presence of the catalysts in question at a temperature within the range of 210° C. and 285° C. and preferably between 225° C. and 270° C.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

In the reaction of ethylene with oxygen to ethylene oxide, the ethylene is present in at least a double molecular quantity, but the quantity of ethylene employed is often much higher. The conversion is therefore calculated according to the quantity of converted oxygen in the reaction and we therefore speak of oxygen conversion. This oxygen conversion is dependent on the temperature of the reaction is a measure of the activity of the catalyst The values $T_{30}$, $T_{40}$ and $T_{50}$ refer to the temperatures at 30 mol%, 40 mol% and 50 mol% conversion respectively of the oxygen in the reactor. The temperatures are generally higher for a higher conversion and are highly dependent on the catalyst employed and the reaction conditions. In addition to these T-values, one also comes across selectivity values, which indicate the molar percentage of ethylene oxide in the reaction mixture obtained. The selectivity is indicated as $S_{30}$, $S_{40}$ or $S_{50}$, which refers to the selectivity at 30%, 40% or 50% oxygen conversion respectively.

The concept "stability of a catalyst" cannot be expressed directly. Stability measurements require trails of long duration. For measuring the stability, the applicant has a number of tests which are carried out under extreme conditions with space velocities of 30,000 liter (liter catalyst)$^{-1}$h$^{-1}$, where liters of throughput gas are understood to be liters STP (standard temperature and pressure). This space velocity is many times higher than the space velocity in commercial processes, which may range from 2800 to 8000 GHSV. The test is carried out for about 1 month. The above-mentioned T- and S-values are measured during the entire period of the test. After the test has been broken off, the total quantity of ethylene oxide per ml catalyst is determined. The difference in selectivity and activity (over start-up selectivity and activity) is calculated for a catalyst which would have produced 1000 gram ethylene oxide per ml catalyst. A new catalyst is considered to be more stable than a known catalyst if the differences in the T- and S-values of the new catalyst and less than those of the standard catalyst which is present during each test. The stability tests are carried out at 35% oxygen conversion.

EXAMPLE 0.99 g cesium chloride and 9.46 g AlCl$_3$.6H$_2$O dissolved in 160 ml water was mixed with 135.0 g Kaiser aluminum oxide (Al$_2$O$_3$.H$_2$O) by adding the cesium chloride-aluminum chloride solution to the aluminum oxide, and the mixture was kneaded for 8 minutes in a masticator and extruded. The resulting shaped pieces were dried for 1 hour at 120° C. and subsequently calcined at progressively higher temperatures. Calcination was started with the temperature rising at a rate of 200° C./h to 500° C. Calcination was then continued for 1 hour at 500° C., after which the temperature was raised in 2 hours to 1400° C., then continued for 1 hour at 1400° C. Finally, the temperature was raised in 2 hours to 1600° C. and calcination was continued for 6 hours at 1600° C. The pore volume of the shaped aluminum oxide pieces was 0.55 ml.g$^{-1}$ and the average pore diameter was 1.8 μm. The weighed-out cesium/aluminum atom ratio was 0.003. The resulting shaped pieces were impregnated with an aqueous solution of silver oxalate, to which cesium hydroxide was added. The impregnation was carried out for 10 minutes under vacuum, after which the shaped pieces were separated from the solution and placed in a hot air stream at a temperature of 250°-270° C. for 10 minutes in order to convert the silver salt to silver. The aqueous solution of silver oxalate was a 28 wt % Ag-containing aqueous solution in which the silver oxalate was complexed with ethylene diamine and to which solution cesium hydroxide was added. After the hot air treatment the thus impregnated shaped pieces contained 20.7 wt % Ag (calculated on total catalyst) and 350 parts by weight of cesium per million parts by weight of total catalyst.

The catalyst obtained was then tested. A cylindrical steel reactor was a length of 15 cm and a cross-section of 3 mm was filled entirely with catalyst particles of about 0.3 mm in size. The reactor was placed in a bath in which silicon/aluminum particles were present in a fluidized state. A gas mixture with the following composition was passed through the reactor: 30 mol% ethylene, 8.5 mol% oxygen, 7 mol% carbon dioxide and 54.5 mol% nitrogen and 7 parts per million parts of gas of vinyl chloride as moderator. The space velocity was 30,000 1 1$^{-1}$h$^{-1}$. The pressure was 15 bar and the temperature was dependent on the set oxygen conversion. The measuring equipment was connected to the reactor and to a computer such that the conversion and the temperature could be accurately controlled. The concentrations of the reaction components were determined with the aid of gas chromatography and mass spectrometry. The stability test was carried out at an oxygen conversion of 35%.

The reaction temperature at 35% oxygen conversion was determined during the entire duration of the test. The selectivity in respect of ethylene oxide was also determined. After at least 30 days the test was broken off and the total quantity of ethylene oxide produced per ml catalyst was determined. From the measured reaction temperatures, starting at the beginning of the reaction, the increase in reaction temperature was calculated in °C. for the moment at which 1000 g ethylene oxide per ml catalyst would have been produced ($\Delta T_{35}^{1000}$). From the measured selectivities, starting at the beginning of the reaction, the selectivity decrease in % mol was calculated for the moment at which 1000 g ethylene oxide per ml catalyst would have been produced ($\Delta S_{35}^{1000}$). The same measurements and calculations was carried out for a standard catalyst in the test. The standard catalyst was S839, a commercial ethylene oxide catalyst being sold by Shell Oil Company and shell International Chemical Company.

The table shows the $\Delta S_{35}^{1000}$ and $\Delta T_{35}^{1000}$, expressed in percentages of the $\Delta S_{35}^{1000}$ and $\Delta T_{35}^{1000}$ respectively of the standard silver catalyst, that is $\Delta S_{35}^{1000}$ for Example 1 divided by $\Delta S_{35}^{1000}$ for S839 times 100%, etc.

| Example | Catalyst wt. % Ag | ppm Cs | $\Delta S_{35}^{1000}$ % of S839 | $\Delta T_{35}^{1000}$ % of 839 |
| --- | --- | --- | --- | --- |
| 1 | 20.7 | 350 | 35 | 45 |
| Comparison | S839 | | 100 | 100 |

We claim:

1. A process for the preparation of a silver-containing catalyst suitable for the oxidation of ethylene to ethylene oxide which comprises:
    (a) mixing an aluminum oxide with water and with a salt of an alkali metal and with aluminum fluoride and/or aluminum chloride,
    (b) calcining the mixture to obtain an alkali enriched aluminum carrier,
    (c) applying a solution of a silver compound to the alkali enriched alumina carrier and converting said silver compound to metallic silver.

2. The process according to claim 1, wherein the alumina is anhydrous or hydrated alumina.

3. The process according to claim 1, wherein the sale of the alkali metal is a fluoride, nitrate, chloride or a sulphate.

4. The process according to claim 1, wherein the alkali metal is cesium.

5. The process according to claim 1, wherein the alumina is mixed with a quantity of alkali metal salt such that the atom ratio of alkali metal/aluminum is between 0.001 to 0.01.

6. The process according to claim 1, wherein the calcination under (b) is carried out at a temperature of between 1200° C. and 1700° C.

7. The process according to any one of the claims 1-6, wherein alumina is mixed with water, a salt of an alkali metal and aluminum fluoride or aluminum chloride, the resulting mixture is extruded to shaped carrier particles, which latter are calcined.

8. The process according to claim 1, wherein the calcined alkali enriched alumina carrier is impregnated with a solution of a silver compound sufficient to apply 1 to 25 percent by weight of silver, calculated on the weight of total catalyst on the carrier, and the precipitated silver compound is reduced to metallic silver.

9. The process according to any one of claims 1 to 8, wherein additionally an alkali metal promoter is applied.

10. The process according to claim 9, wherein besides the silver compound applied to the carrier, a sufficient quantity of one or more compounds of the alkali metals potassium, rubidium or cesium is applied to the carrier to deposit between 20 and 1000 parts by weight of the alkali metal (measured as the metal) per million pars by weight of total catalyst.

11. The process according to claim 10 wherein the alkali metal is cesium.

12. A process for the preparation of a silver-containing catalyst suitable for the oxidation of ethylene and ethylene oxide which comprises:
    (a) mixing an anhydrous or hydrated alumina with water, cesium fluoride, nitrate or chloride and with aluminum fluoride or chloride wherein the atom ratio of cesium/aluminum (oxide) is between about 0.001 and about 0.01 and the atom ratio of aluminum (chloride or fluoride)/aluminum (oxide) ranges from about 0.01 to about 0.1,
    (b) shaping and calcining the mixture of (a) at a temperature ranging from about 1200° C. to about 1700° C. to obtain an alkali metal enriched alumina carrier, and
    (c) applying a solution of a silver compound and a cesium promoter sufficient to apply from about 1 to about 25 percent by weight of the total catalyst of silver and from about 20 to about 1000 ppm by weight of the total catalyst of cesium promoter and converting said silver compound to metallic silver.

13. In a catalyst for the production of ethylene oxide from ethylene and molecular oxygen which comprises silver and an alkali metal promoter supported on a carrier, the improvement wherein the carrier is prepared by a process which comprises:
    (a) mixing an aluminum oxide with water and with a salt of an alkali metal and with aluminum fluoride and/or aluminum chloride,
    (b) calcining the mixture to obtain an alkali enriched alumina carrier,
    (c) applying a solution of a silver compound and an alkali metal promoter to the alkali enriched alumina carrier and converting said silver compound to metallic silver.

14. The catalyst according to claim 13, wherein the alumina is anhydrous or hydrated alumina.

15. The catalyst according to claim 13, wherein the salt of the alkali metal is a fluoride, nitrate, chloride or a sulphate.

16. The catalyst according to claim 13, wherein the alkali metal (in step a) is cesium.

17. The catalyst according to claim 13, wherein the aluminum oxide is mixed with a quantity of alkali metal salt such that the atom ratio of alkali metal/aluminum (oxide) is between 0.001 to 0.01.

18. The catalyst according to claim 13, wherein the calcination under (b) is carried out at a temperature of between 1200° C. and 1700° C.

19. The catalyst according to claim 13, wherein aluminum oxide is mixed with water, a salt of an alkali metal and aluminum fluoride or aluminum chloride, the resulting mixture is extruded to shaped carrier particles, which latter are calcined.

20. The catalyst according to claim 13, wherein the calcined alkali enriched alumina carrier is impregnated with a solution of a silver compound sufficient to apply 1 to 25 percent by weight of silver, calculated on the weight of total catalyst, on the carrier, and the precipitated silver compound is reduced to metallic silver.

21. The catalyst according to any of claims 13-20, wherein the alkali metal promoter is selected from potassium, rubidium, cesium and mixtures thereof.

22. The catalyst according to claim 21, wherein the alkali metal promoter is cesium.

23. A catalyst for the production of ethylene oxide from ethylene and molecular oxygen which comprises about 1-25 wt % silver (basis total catalyst) and about 20-1000 ppm of cesium promoter (basis total catalyst) supported on a carrier wherein the improvement comprises preparing the carrier by a process which comprises:
    (a) mixing an anhydrous or hydrated alumina with water, cesium fluoride, nitrate, chloride or sulphate and with aluminum fluoride or aluminum chloride wherein the atom ratio of cesium/aluminum (oxide) is between about 0.001 and about 0.01 and the atom ratio of aluminum (chloride or fluoride)/aluminum (oxide) ranges from about 0.01 to about 0.1,
    (b) shaping the mixture of (a),
    (c) calcining the shaped mixture of (b) at a temperature ranging from about 1200° C. to about 1700° C. to obtain an alkali enriched alumina carrier, and
    (d) applying a solution of a silver compound and a cesium promoter to the alkali enriched alumina carrier and converting said silver compound to metallic silver.

* * * * *